US00RE39387E

(19) United States
(12) Reissued Patent
Shin

(10) Patent Number: US RE39,387 E
(45) Date of Reissued Patent: Nov. 14, 2006

(54) CONTAINER

(75) Inventor: Hyun Woo Shin, Seoul (KR)

(73) Assignee: Oxy Co., Ltd., Seoul (KR)

(21) Appl. No.: 29/159,010

(22) Filed: Mar. 15, 2002

Related U.S. Patent Documents

Reissue of:
(64) Patent No.: Des. 449,102
Issued: Oct. 9, 2001
Appl. No.: 29/130,275
Filed: Sep. 29, 2000

(51) LOC (8) Cl. ..... 23-04
(52) U.S. Cl. ..... D9/529
(58) Field of Classification Search ..... D9/432, D9/550, 338, 529, 549, 430, 729, 728; 220/DIG. 13; D23/355, 366–369; 46/151, 154, 133
See application file for complete search history.

(56) References Cited

U.S. PATENT DOCUMENTS

D366,521 S * 1/1996 Wijaranakula ..... D23/366
D414,689 S * 10/1999 Ruello ..... D9/338
D455,647 S * 4/2002 Cummings ..... D9/338

* cited by examiner

*Primary Examiner*—Lisa Lichtenstein
(74) *Attorney, Agent, or Firm*—Howard & Howard

(57) CLAIM

An ornamental design for a [refrigerator deodorant] container, as shown and described.

DESCRIPTION

FIG. 1 is a perspective view of a container [for a deodorant for a refrigerator];
FIG. 2 is a front elevational view thereof;
FIG. 3 is a rear elevational view thereof;
FIG. 4 is a side elevational view thereof;
FIG. 5 is a side elevational view thereof of the side opposite to that shown in FIG. 4;
FIG. 6 is a top plan view thereof; and,
FIG. 7 is a bottom plan view thereof.

1 Claim, 3 Drawing Sheets

Figure 1:
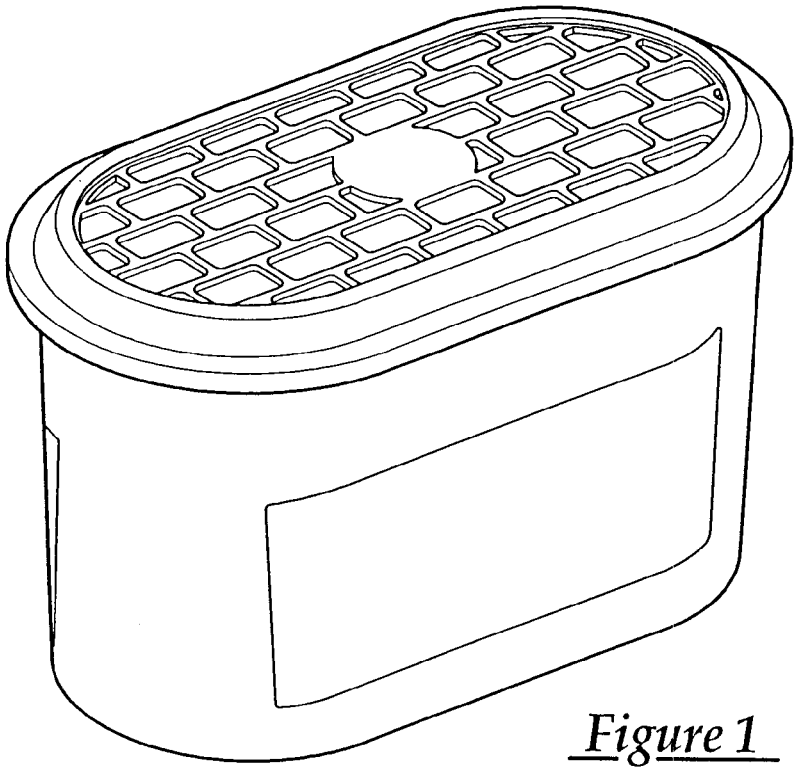
Figure 2:
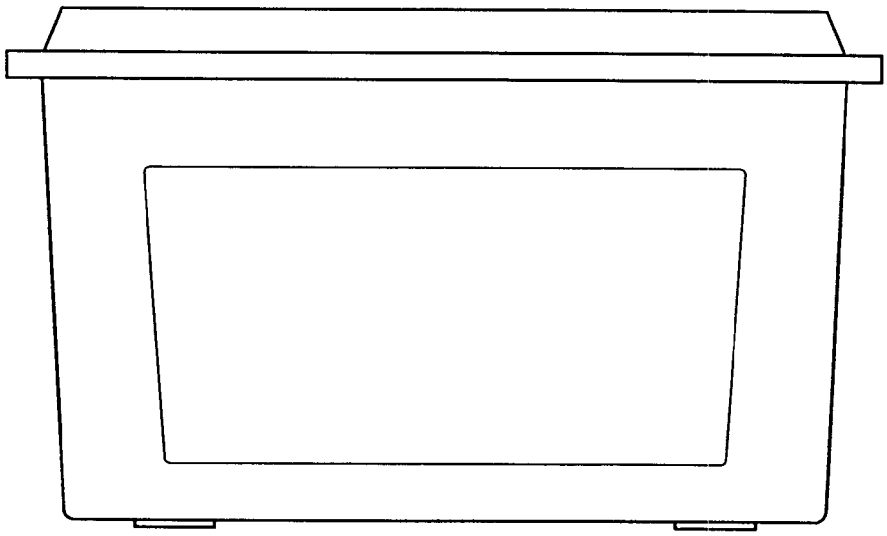
Figure 3:
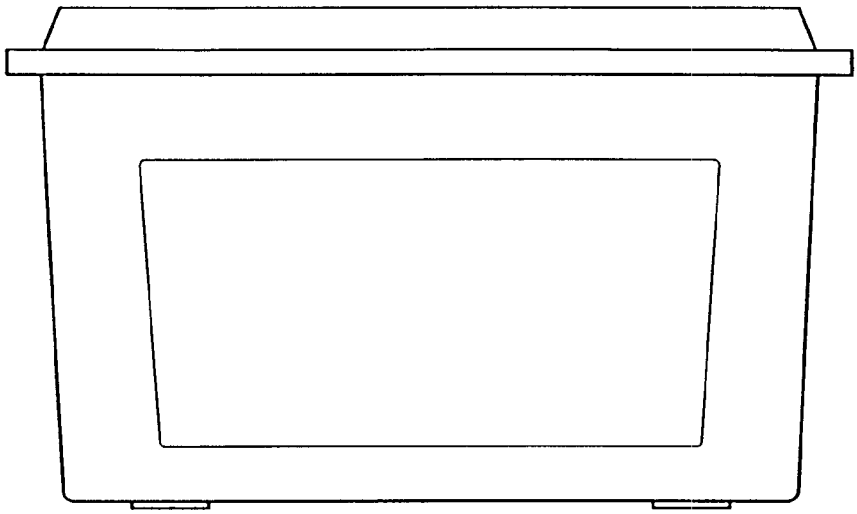
Figure 4:
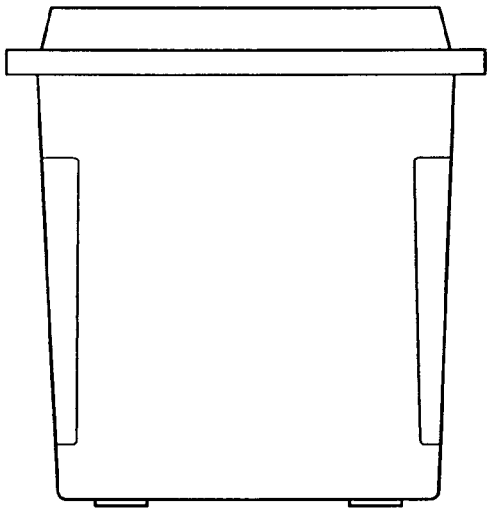
Figure 5:
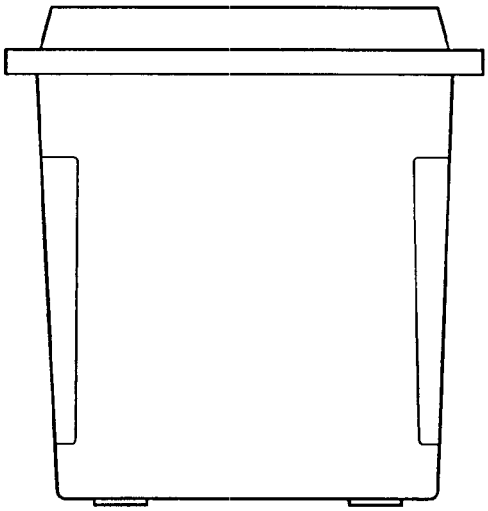
Figure 6:
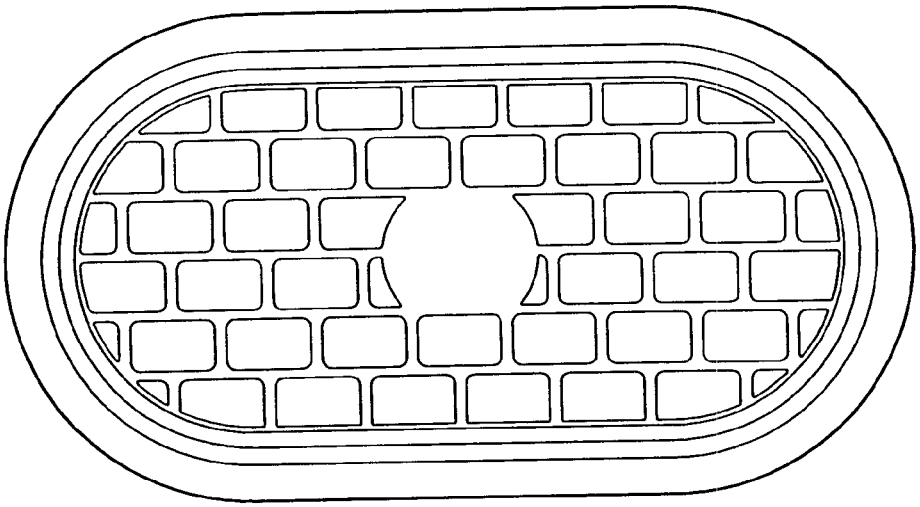
Figure 7:
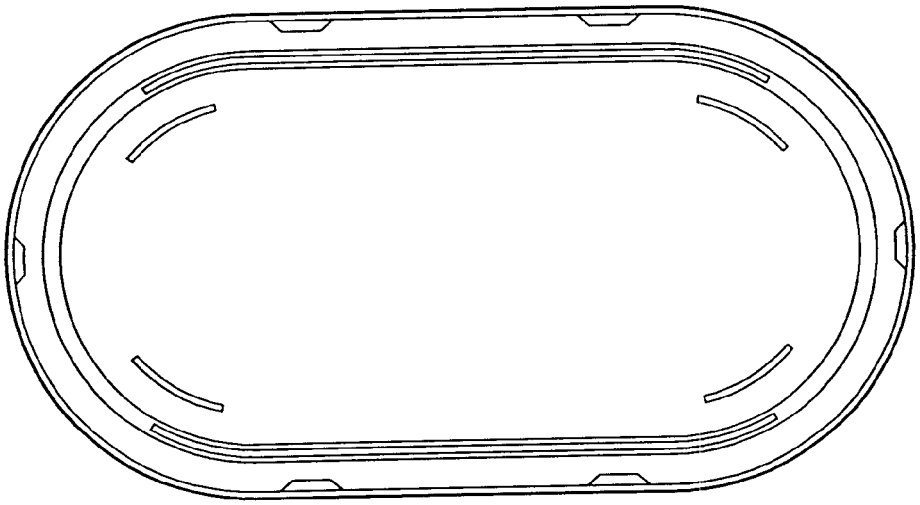

Matter enclosed in heavy brackets [ ] appears in the original patent, but forms no part of this reissue; matter printed in italics indicates the additions made by reissue.